United States Patent
Motta et al.

(10) Patent No.: US 10,436,731 B2
(45) Date of Patent: Oct. 8, 2019

(54) LOW HEAT TRANSFER ENCAPSULATION FOR HIGH SENSITIVITY AND LOW POWER ENVIRONMENTAL SENSING APPLICATIONS

(71) Applicant: Apple Inc., Cupertino, CA (US)

(72) Inventors: Paulo S. Motta, San Jose, CA (US); Roberto M. Ribeiro, San Jose, CA (US); Richard Yeh, Los Altos, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 16/048,139

(22) Filed: Jul. 27, 2018

(65) Prior Publication Data

US 2019/0033242 A1    Jan. 31, 2019

Related U.S. Application Data

(60) Provisional application No. 62/538,585, filed on Jul. 28, 2017.

(51) Int. Cl.
*G01N 27/12*    (2006.01)
*B81B 7/00*    (2006.01)

(52) U.S. Cl.
CPC .......... *G01N 27/12* (2013.01); *B81B 7/0061* (2013.01); *B81B 7/0087* (2013.01); *G01N 27/123* (2013.01); *G01N 27/128* (2013.01); *B81B 2201/0214* (2013.01)

(58) Field of Classification Search
CPC .. G01N 27/125; G01N 27/128; B81B 3/0089; B81B 7/0087; B81B 2201/0214
USPC ....................................................... 257/414
See application file for complete search history.

(56) References Cited

U.S. PATENT DOCUMENTS

2015/0021716 A1*    1/2015 Lee ...................... G01N 27/128
                                                                257/414
2019/0025271 A1*    1/2019 Yan .................... G01N 33/0016

\* cited by examiner

*Primary Examiner* — Caleen O Sullivan
(74) *Attorney, Agent, or Firm* — Morgan, Lewis & Bockius LLP

(57) ABSTRACT

A miniature gas sensing device includes a silicon-based substrate including an opening. A first membrane is formed over the silicon-based substrate and a first portion of the first membrane covers the opening. A gas sensing layer is formed over a number of electrodes disposed over a first surface of the first portion of the first membrane and one or more heating elements. A permeable enclosure encapsulating the gas sensing layer can maintain thermal energy density over the gas sensing layer at a level sufficient to destroy a target gas to allow measuring a zero baseline.

20 Claims, 7 Drawing Sheets

LOW HEAT TRANSFER ENCAPSULATION FOR HIGH SENSITIVITY AND LOW POWER ENVIRONMENTAL SENSING APPLICATIONS

CROSS-REFERENCE TO RELATED APPLICATIONS

This application claims the benefit of priority under 35 U.S.C. § 119 from U.S. Provisional Patent Application 62/538,585 filed Jul. 28, 2017, which is incorporated herein by reference in its entirety.

TECHNICAL FIELD

The present description relates generally to sensors, and more particularly, to low heat transfer encapsulation for high sensitivity and low power environmental sensing applications.

BACKGROUND

Miniature gas sensors for consumer electronics represent a technology category that could enable upcoming features and/or products in applications such as environmental and health monitoring, smart homes, internet of things (IoT), and a number of other applications. Metal oxide (MOX) gas sensors are among the most promising technologies to be integrated with consumer electronic devices, due to their small size, low power consumption, compatibility with semiconductor fabrication processes and relatively simple architecture.

An issue with many environmental sensors is the baseline drift, where the baseline may change with an environmental condition such as variations in chemistry, temperature or other conditions of the environment. The baseline drift of a sensor can be addressed, for example, by a suitable compensation. A drift in sensitivity of a sensor, however, can be major issue that can drastically affect the measurement results. Therefore, environmental sensors capable of performing absolute measurements are desired.

BRIEF DESCRIPTION OF THE DRAWINGS

Certain features of the subject technology are set forth in the appended claims. However, for purposes of explanation, several embodiments of the subject technology are set forth in the following figures.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without one or more of the specific details. In some instances, structures and components are shown in block diagram form in order to avoid obscuring the concepts of the subject technology.

In one or more aspects of the subject technology, solutions for producing encapsulated low-heat-transfer miniature gas sensors are provided. The gas sensors of the subject technology include advantageous features such as improved stability, longer lifetime, enhanced sensitivity drift prevention, and capability to perform absolute measurements at part per million (ppb) levels. The disclosed solutions can be employed for long-term implementation of environmental and health sensing and hazardous gas species detection in applications such as smart homes, internet of things (IoT), and other applications. The subject technology enables a differential measurement including a measurement of the baseline. The baseline measurement is performed after the target gas is destroyed and does no longer exist in the sensor cavity.

Figure 1:
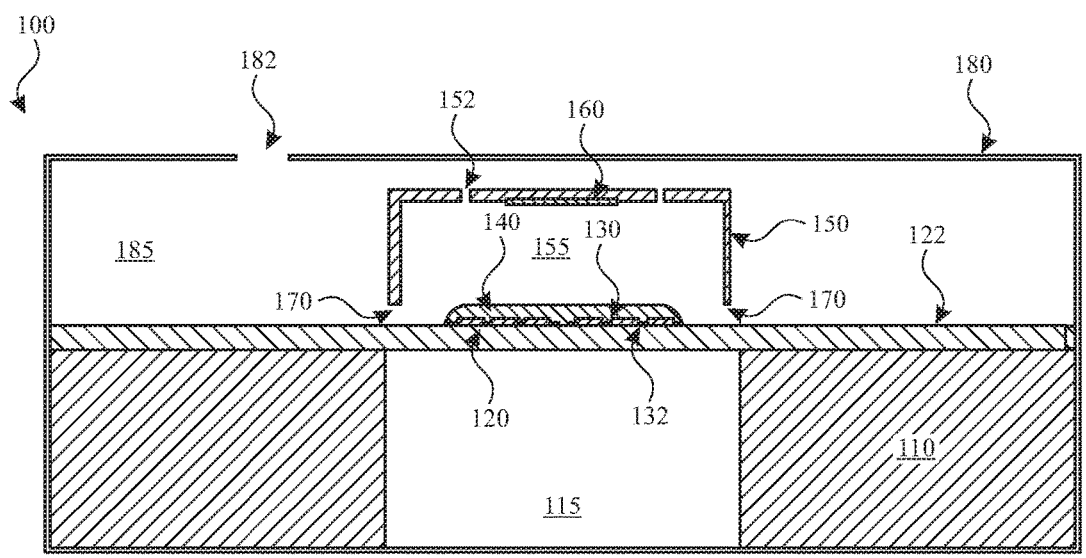
FIG. 1 is a schematic diagram illustrating an example of an encapsulated low-heat-transfer miniature gas sensing device, in accordance with one or more aspects of the subject technology.

FIG. 1 is a schematic diagram illustrating an example of an encapsulated low-heat-transfer miniature gas sensing device 100, in accordance with one or more aspects of the subject technology. The encapsulated low-heat-transfer miniature gas sensing device 100 (hereinafter "gas sensor 100") includes a silicon-based substrate 110 including an opening 115, a first membrane 120, a gas sensing layer 140 formed over a number of electrodes 130 disposed over the membrane 120, one or more heating elements 132, a permeable enclosure 150 covering the gas sensing layer 140 and a casing 180. The silicon based substrate can be silicon substrates made of a silicon wafer. The electrodes 130 are disposed over a first surface 122 (e.g., top surface) of a first portion of the first membrane 120 that covers the opening 115.

In some implementations, the electrodes 130 can be made of metals such as copper (Cu), aluminum (Al), silver (Ag), graphite (C), titanium (Ti), gold (Au), or other suitable metals, alloys or compounds. The electrodes 130 may be plated on the first membrane 120 in the form of a number of strips, for example, with suitable dimensions and distances.

In some implementations, the gas sensing layer 140 is made of a metal oxide, for example, a granular metal oxide semiconductor material including tin dioxide ($SnO_2$), tungsten trioxide ($WO_3$) and/or zinc oxide (ZnO2). The gas sensing layer 140 may detect a target gas and convert the concentration of the gas target into an electrical resistance. The gas sensing layer 140 is formed on the electrodes 130, which are capable of sensing the electrical resistance that represents the target gas concentration.

The permeable enclosure 150 encapsulates the gas sensing layer 140 and can maintain thermal energy density over the gas sensing layer 140 at a sufficiently high level to destroy (e.g., decompose) a target gas (e.g., ozone) to allow measuring a zero baseline. The target gas may be a different gas depending on the application. For example, the target gas may be volatile organic compounds (VOCs), which can include elements such as hydrogen, oxygen, fluorine, chlorine, bromine, sulfur and nitrogen. VOCs can be found, for example, in fragrances, detergents and gassing from burning furniture and hardwood floors including formaldehyde or other chemicals. In other implementations, the gas sensor 100 may be configured to sense other target gases.

The permeable enclosure 150 can include one or more restricted flow openings (holes) 152. In some implementations, one or more of the restricted flow openings 152 may include a shutter valve mechanism. The shutter valve mechanism may be operable to at least partially open or close the restricted flow openings 152. The shutter valve mechanisms can be controlled by a microcontroller or a general processor, for example, of a host device (e.g., a smart phone or a smart watch) with which the gas sensor 100 is integrated. In some implementations, the gas sensor 100 may include one or more auxiliary heating elements 160. The auxiliary heating elements 160 can be on built (e.g., deposited) over an external surface of the permeable enclosure 150, in some implementations. The permeable enclosure 150 can include openings 170 (e.g., notches) made at a lower portion of the permeable enclosure 150 near the first membrane 120. The encapsulation by the permeable enclosure 150, the heating elements 132 and the (optional) auxiliary heating elements 160 can facilitate providing a high temperature (e.g., within a range of about 150-300° C.) environment inside a first cavity 155 of the permeable enclosure 150. The high temperature is sufficient to cause the ozone target gas to thermally decompose so that a concentration of the ozone gas is practically reduced to approximately zero. This allows the gas sensor layer 140 to register a zero target gas level. The high temperature for causing thermal decomposition of other target gases can be different than for ozone.

In some implementations, the heating elements 132 and the auxiliary heating elements 160 are micro electromechanical system (MEMS) hotplates and can include titanium nitride, which is compatible with complementary metal-oxide semiconductor (CMOS) process and has a high melting point (e.g., 2950° C.), although other suitable metals may be used. The heating elements 132 and the auxiliary heating elements 160 can be independently controlled (e.g., by a microcontroller or a general processor) and can be used to regulate the temperature of the gas sensing layer 140 and the cavity 155. For example, the temperature of the gas sensing layer 140 may be set to nominal temperature (e.g., within a range of about 250-350° C.) by the heating elements 132. In some aspects, the microcontroller or the general processor can be in the host device. In some aspects, the heating elements 132 can be used to regenerate the sensing capabilities of the gas sensing layer 140.

The openings 170 allow fresh target gas to enter the first cavity 155 for target gas concentration measurement phase. In some implementations, the casing 180 may be a metallic casing, for example, made of aluminum, stainless steel, titanium, or other metals or alloys. The casing 180 includes an opening (hole) 182 for allowing gas exchange between a second cavity 185 and the outside environment. In the following sections of the disclosure, various implementations of the miniature gas sensing device of the subject technology are disclosed.

Figure 2A:
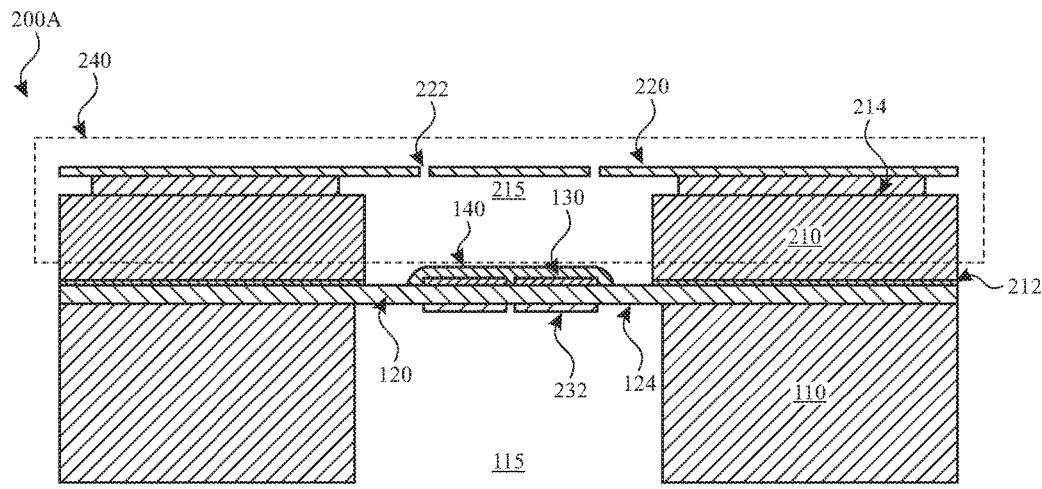
FIGS. 2A, 2B and 2C are schematic diagrams illustrating examples of an encapsulated low-heat-transfer miniature gas sensing device manufacturable by integrated circuit (IC) fabrication processes, in accordance with one or more aspects of the subject technology.
Figure 2B:
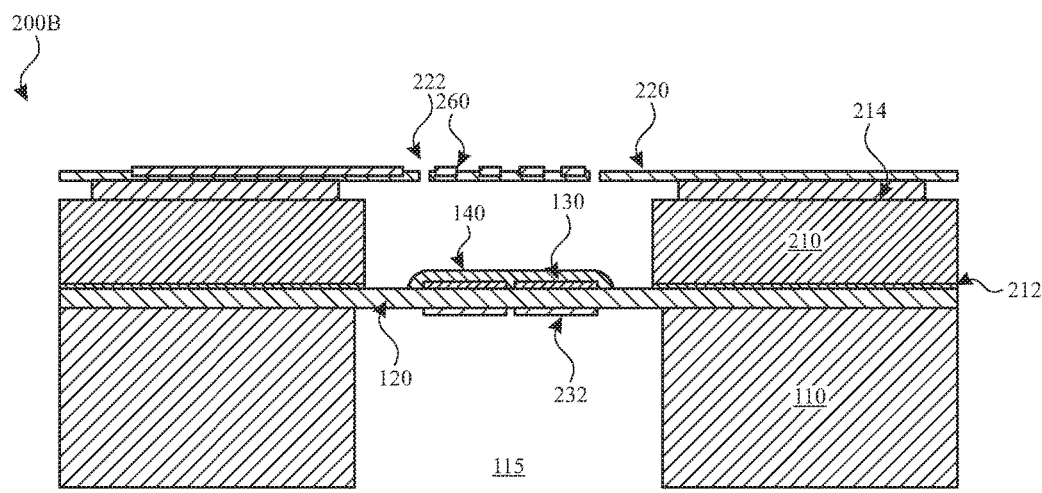
Figure 2C:
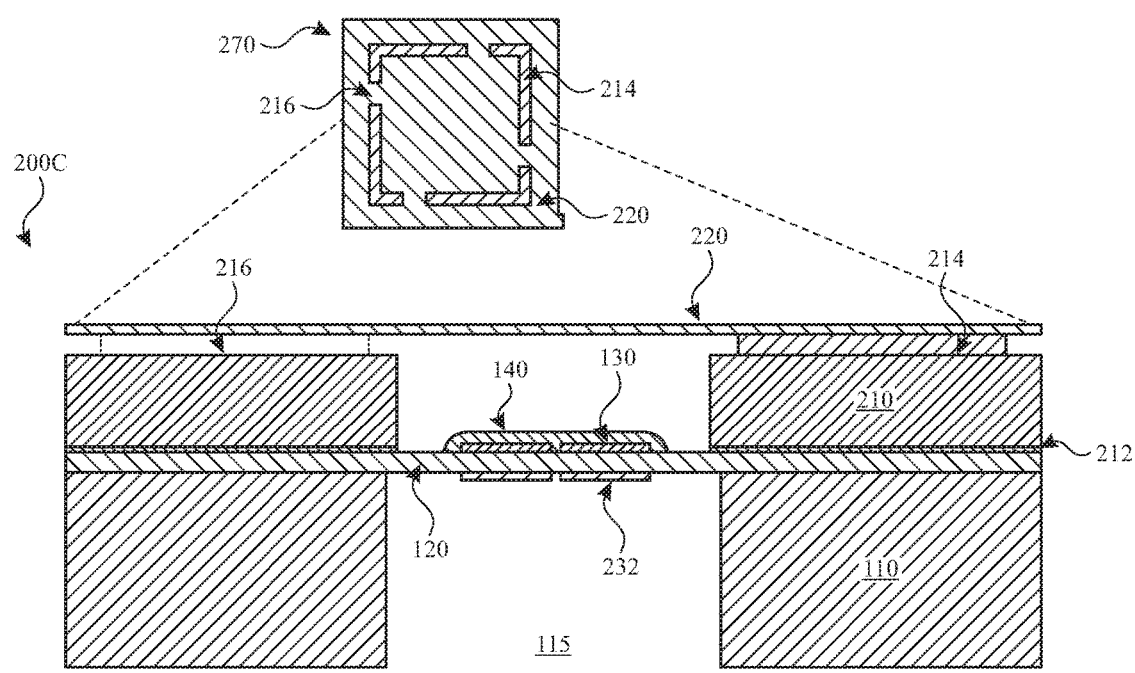

FIGS. 2A, 2B and 2C are schematic diagrams illustrating examples of an encapsulated low-heat-transfer miniature gas sensing device manufacturable by integrated circuit (IC) fabrication processes, in accordance with one or more aspects of the subject technology. The example encapsulated low-heat-transfer miniature gas sensing device 200A (hereinafter "gas sensor 200A") shown in FIG. 2A is similar to the gas sensor 100 of FIG. 1, except that the casing 180 is not shown (or does not exist), the permeable enclosure 150 of FIG. 1 is implemented by the permeable enclosure 240, and the heating elements 232 are built on a second surface 124 of the first membrane 120. The structure and functionalities of the substrate 110, the first membrane 120, the electrodes 130 and the gas sensor layer 140 are as described with respect to FIG. 1. The structure and functionalities of the heating elements 232 are the similar to the heating elements 132 of FIG. 1.

In some implementation, the permeable enclosure 240 is built separately and is bonded to the first membrane 120 using a bonding layer 212 (e.g., a cap bonding frame made of, for example, epoxy). In some implementation, the permeable enclosure 240 includes a sidewall 210, a bond frame 214 and a permeable lid 220 including one or more restricted flow holes 222. In some implementations, the restricted flow holes 222 may include shutter valve mechanisms operable to at least partially open or close the restricted flow holes 222. The shutter valve mechanisms can be controlled by a microcontroller or a general processor, for example, of a host device (e.g., a smart phone or a smart watch).

In some implementations, the permeable enclosure 240 can be fabricated by employing fabrication techniques used in the integration circuit (IC) fabrication technology. For example, the sidewall 210 can be made of a glass wafer that is predrilled to form the cavity 215 and subsequently ground to a suitable thickness (e.g., within a range of about 40-60 µm). The sidewall width (e.g., thickness in the horizontal direction) of the glass sidewall 210 is much higher (e.g., within a range of about 200-500 µm) than the thickness of the sidewalls of the permeable enclosure 150 of FIG. 1 and is significantly more effective in providing low heat transfer and thermal isolation. The thermal isolation allows heating the cavity 155 with lower power consumption, thus making the gas sensor 100 a lower power device.

The bond frame 214 can be a glass-to-silicon bond formed, for example, by using a known anodic bonding process. In one or more implementations, the permeable lid 220 is a silicon oxide layer that is first deposited on a silicon wafer (e.g., a handle wafer) and patterned and etched to create the restricted flow holes 222. The silicon wafer is then ground off from the silicon oxide layer.

The example encapsulated low-heat-transfer miniature gas sensing device 200B (hereinafter "gas sensor 200B") shown in FIG. 2B is similar to the gas sensor 200A of FIG. 2A, except for an auxiliary heating elements 260 formed on top surface of the permeable lid 220, as shown in FIG. 2B. The structure and functionalities of the auxiliary heating elements 260 is similar to those of the auxiliary heating elements 160 of FIG. 1, described above.

The example encapsulated low-heat-transfer miniature gas sensing device 200C (hereinafter "gas sensor 200C") shown in FIG. 2C is similar to the gas sensor 200A of FIG. 2A, except that the permeable lid 220 does not include the restricted flow holes 222 of FIG. 2A and includes, instead, an opening 216. The opening 216 can be formed at one or more locations (e.g., near for corners) on the bond frame 214, as shown in the top view 270 of the gas sensor 200C. In the example implementation shown in FIG. 200C and top view 270, the top view of the gas sensor 200C has a square shape, but the subject technology is not limited to this shape.

Figure 3A:
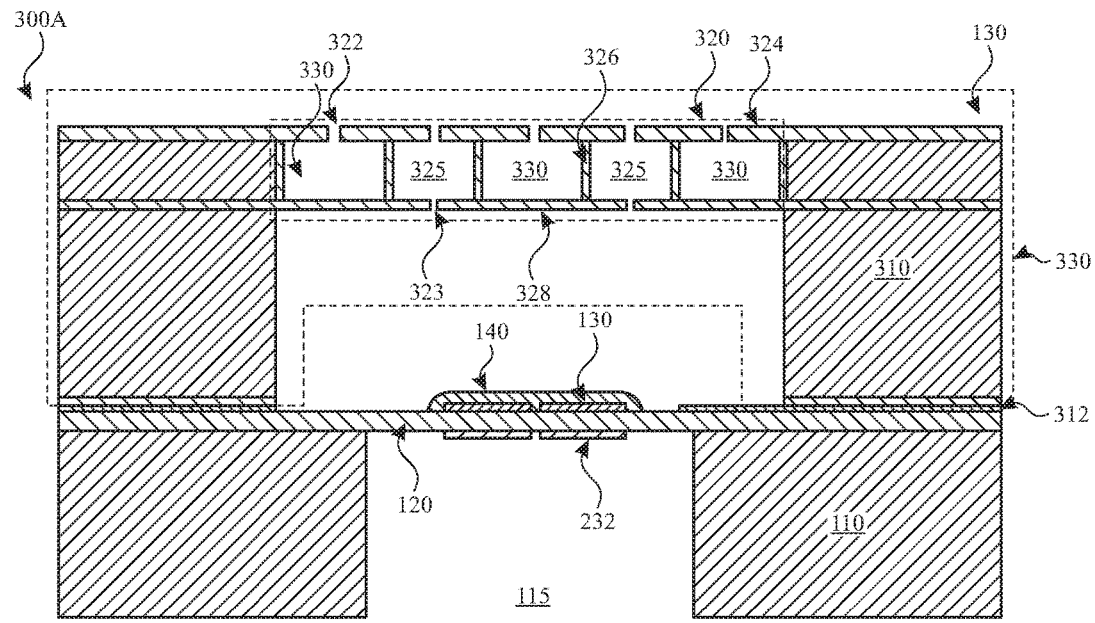
FIGS. 3A-3B are schematic diagrams illustrating examples of an encapsulated low-heat-transfer double hollow membrane miniature gas sensing device, in accordance with one or more aspects of the subject technology.
Figure 3B:
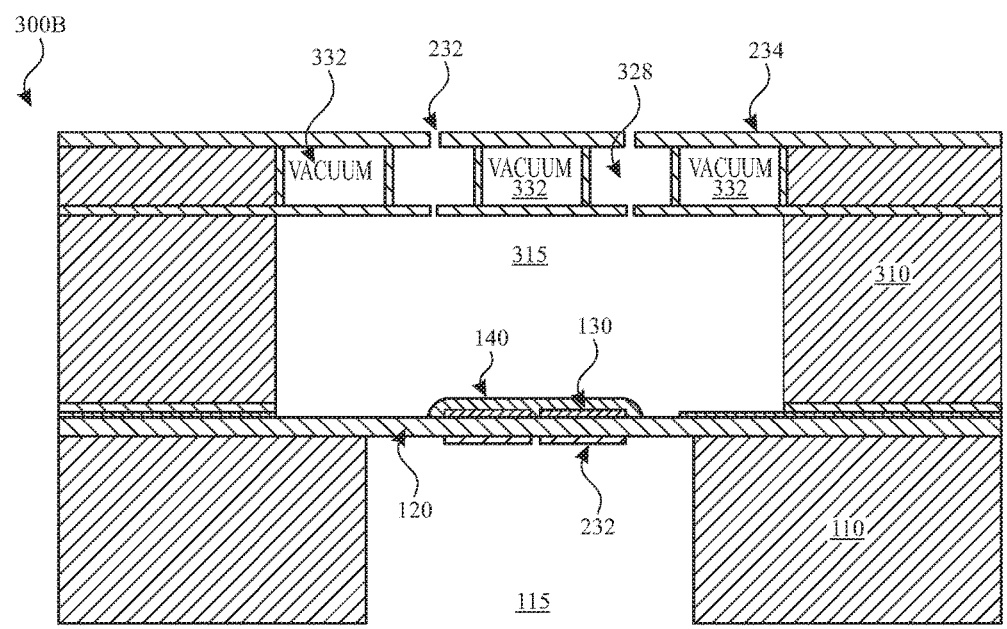

FIGS. 3A-3B are schematic diagrams illustrating examples of an encapsulated low-heat-transfer double hollow membrane miniature gas sensing device, in accordance with one or more aspects of the subject technology. The example encapsulated low-heat-transfer double hollow membrane miniature gas sensing device 300A (hereinafter "gas sensor 300A") shown in FIG. 300A is similar to the gas sensor 200A of FIG. 2A, except that the permeable enclosure 240 of FIG. 2A is replaced with a permeable enclosure 330. The structure and functionalities of the substrate 110, the first membrane 120, the electrodes 130 and the gas sensor layer 140 are as described with respect to FIG. 1. The permeable enclosure 330 includes a double hollow membrane 320 and a sidewall 310. The double hollow membrane 320 includes number of cavities separated by inner walls 326. One or more of the cavities have one or more holes. For example, each of the cavities 330 has one hole on a top layer 324 and each of the cavities 325 has two holes, one hole (e.g., 322) on the top layer 324 and another hole (e.g., 323) on a bottom layer 328.

In some implementations, the permeable enclosure 330 is separately fabricated by employing IC fabrication techniques and is attached to the first membrane 120 using a bonding layer 312 similar to the bonding layer 212 of FIG. 2A.

The example encapsulated low-heat-transfer double hollow membrane miniature gas sensing device 300B (hereinafter "gas sensor 300B") shown in FIG. 300B is similar to the gas sensor 300A of FIG. 3A, except that some of the cavities (e.g., 332) have no holes and are vacuumed and sealed to provide lower heat transfer resulting in additional thermal isolation. The additional thermal isolation can further cause increasing the temperature of the cavity 315 in the target gas decomposition stage and thereby help with lowering the power consumption of the sensor device. Thus, the gas sensors 300A and 300B can be designed to operate at lower power than the existing miniature gas sensor, while having the additional advantage of absolute target gas concentration.

Figure 4:
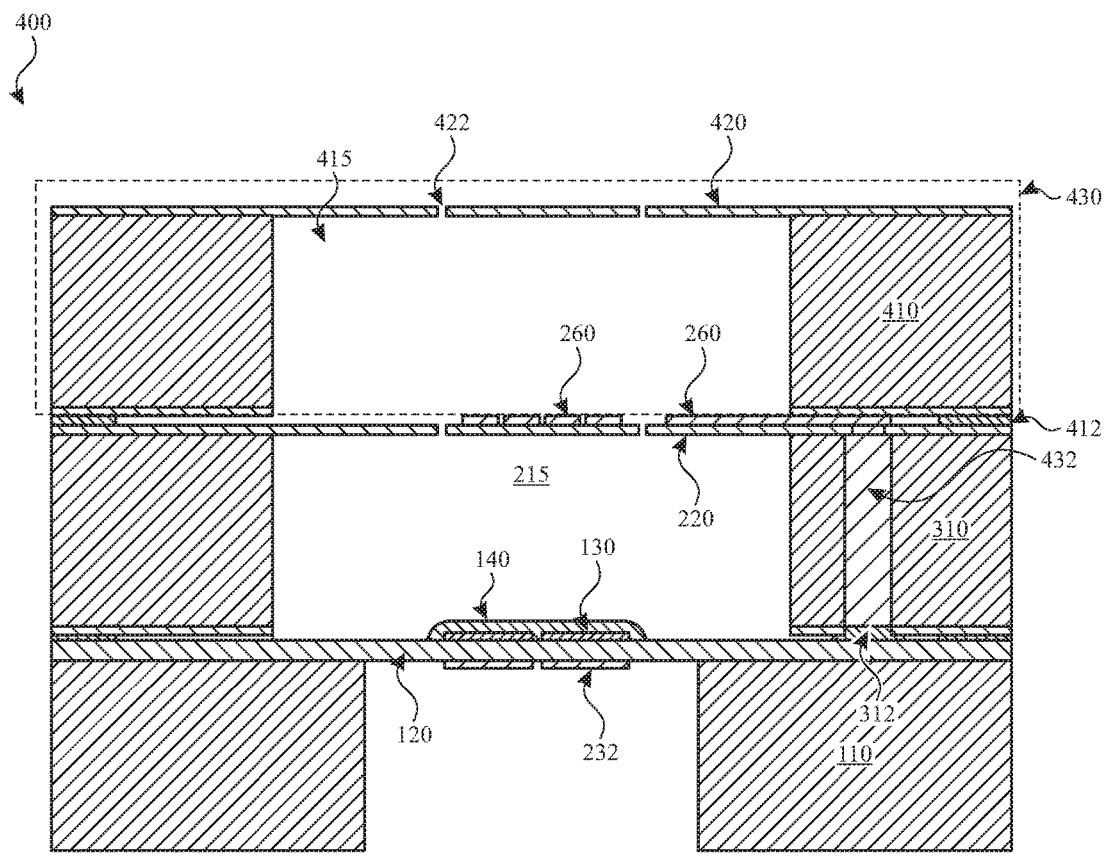
FIG. 4 is a schematic diagram illustrating an example of an encapsulated low heat-transfer double-membrane miniature gas sensing device, in accordance with one or more aspects of the subject technology.

FIG. 4 is a schematic diagram illustrating an example of an encapsulated low heat-transfer double-membrane miniature gas sensing device 400, in accordance with one or more aspects of the subject technology. The example encapsulated low-heat-transfer double-membrane miniature gas sensing device 400 (hereinafter "gas sensor 400") shown in FIG. 4 is similar to the gas sensor 200B of FIG. 2B, except for the additional permeable enclosure 430 and a through-silicon-via (TSV) 432 coupled to an auxiliary heating element 260. The permeable enclosure 430 is similar to the permeable enclosure 240 of FIG. 2 and is fabricated separately, as discussed above with respect to FIG. 2A, and is attached to the permeable lid 220 by using a bonding layer 412. The permeable enclosure 420 includes one or more restricted flow holes 422. In some implementations, the restricted flow holes 422 may include shutter valve mechanisms operable to at least partially open or close the restricted flow holes 422. The shutter valve mechanisms can be controlled by a microcontroller or a general processor, for example, of a host device (e.g., a smart phone or a smart watch). The additional permeable enclosure 430 with a cavity 415 that can be sealed can provide a low heat transfer environment above the auxiliary heating element 260, thereby allowing reaching higher temperatures within the cavity 215 at lower heating power. The auxiliary heating element 260 is coupled through the TSV 432 to a bonding layer 312 that can be wire-bonded to an external pad for provision of power for the auxiliary heating element 260.

Figure 5:
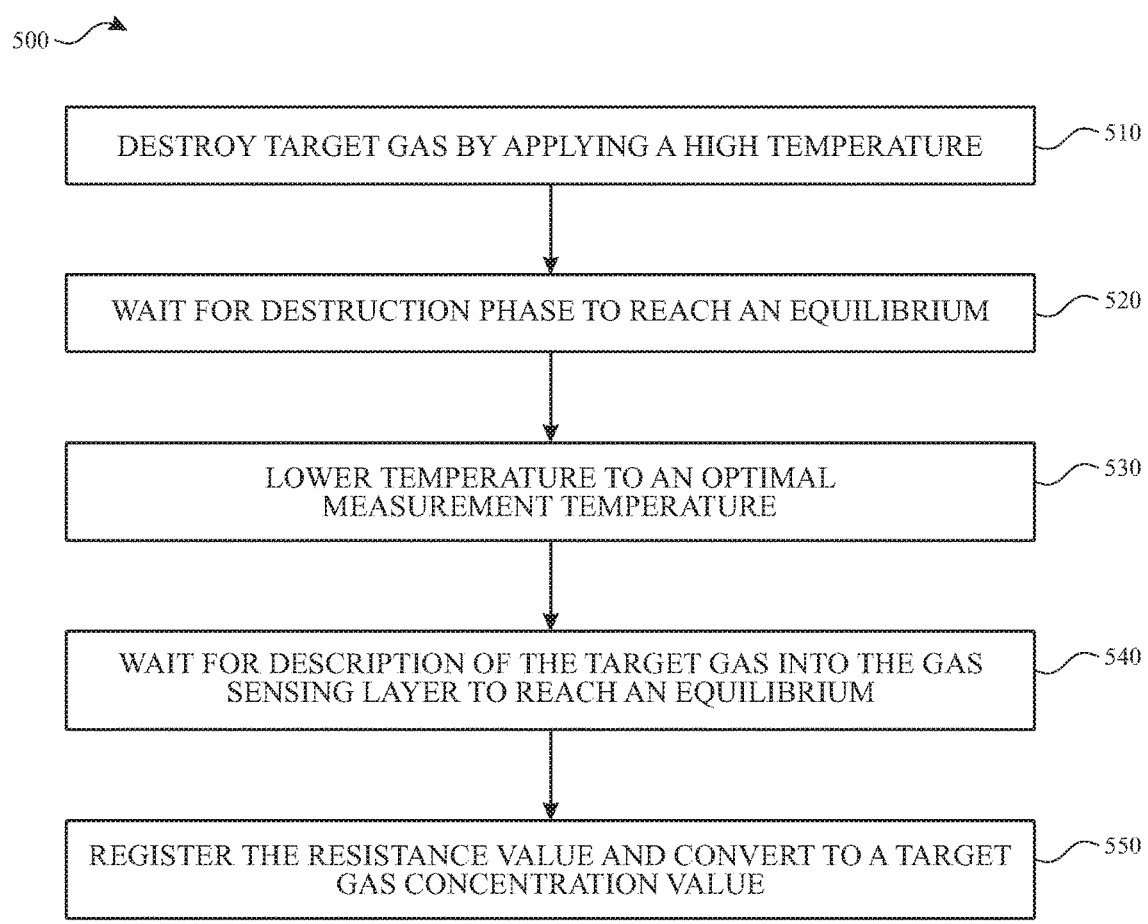
FIG. 5 is a flow diagram illustrating an example of a method of operation of an encapsulated low-heat-transfer miniature gas sensing device, in accordance with one or more aspects of the subject

FIG. 5 is a flow diagram illustrating an example of a method 500 of operation of an encapsulated low-heat-transfer miniature gas sensing device, in accordance with one or more aspects of the subject technology. The operations of the method 500 may be controlled by a microcontroller or a general processor, for example, of a host device (e.g., a smart phone or a smart watch) with which the encapsulated low-heat-transfer miniature gas sensing device (e.g., the gas sensor 100 of FIG. 1) is integrated. The method 500 starts with operation 510, where the target gas (e.g., ozone) is destroyed (e.g., decomposed) by applying a high temperature (e.g., for a 30 second period). The high temperature (e.g., within a range of about 130-260° C.) may be provided by an auxiliary heating element (e.g., 160 of FIG. 1) and maintained by the low-heat-transfer environment provided by a permeable enclosure of the subject technology (e.g., 150 of FIG. 1, 240 of FIG. 2A and 330 of FIG. 3A). In some implementations, the controller may also use the heating elements 132 to further raise the temperature.

At operation 520 the controller waits (does not make any changes) for the environment inside the enclosure cavity (e.g., 155 of FIG. 1) to reach an equilibrium. In the equilibrium, the resistance value of the gas sensing layer (e.g., 140 of FIG. 1), as read by the controller, reaches a steady value (e.g., baseline resistance $R_0$) corresponding to zero concentration of the target gas. The controller then changes the temperature, at operation 530, to an optimal measurement temperature and turns off the auxiliary heating element. The optimal measurement temperature can be different for different gas sensing layers.

At operation 540, the controller waits for desorption of the target gas into the sensing gas layer to reach a state of equilibrium. At the state of equilibrium, the resistance value of the gas sensing layer, as read by the controller, reaches a steady value ($R_g$) corresponding to an actual concentration of the target gas. The controller then registers the resistance value ($R_g$) and converts (at operation 550), the resistance value to a target gas concentration value using a suitable conversion table. The conversion table stored in a memory of the host device can convert a resistance signal (e.g., $R_g/R_0$) to a corresponding value for the target gas concentration. In some implementations the above discussed operations can be performed in a periodic fashion with, for example, 60 seconds of low temperature and 30 seconds of high temperature.

Figure 6:
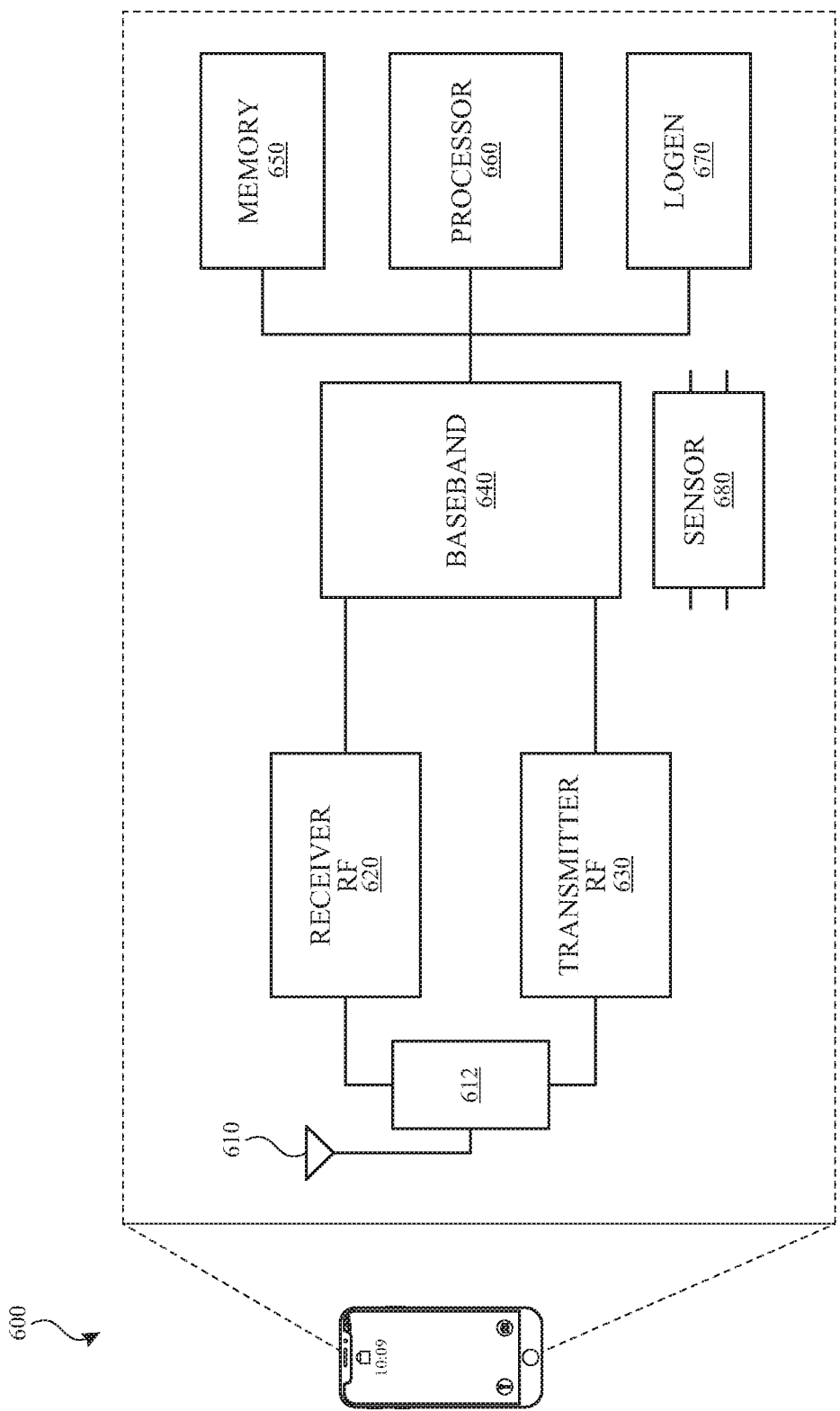
FIG. 6 is a block diagram illustrating an example wireless communication device, within which one or more miniature gas sensors of the subject technology can be integrated.

FIG. 6 is a block diagram illustrating an example wireless communication device, within which one or more miniature gas sensors of the subject technology can be integrated. The wireless communication device 600 may comprise a radio-frequency (RF) antenna 610, a receiver 620, a transmitter 630, a baseband processing module 640, a memory 650, a processor 660, a local oscillator generator (LOGEN) 670, and a sensor 680. In various embodiments of the subject technology, one or more of the blocks represented in FIG. 6 may be integrated on one or more semiconductor substrates. For example, the blocks 620-670 may be realized in a single chip or a single system on a chip, or may be realized in a multi-chip chipset.

The receiver 620 may comprise suitable logic circuitry and/or code that may be operable to receive and process signals from the RF antenna 610. The receiver 620 may, for example, be operable to amplify and/or down-convert received wireless signals. In various embodiments of the subject technology, the receiver 620 may be operable to cancel noise in received signals and may be linear over a wide range of frequencies. In this manner, the receiver 620 may be suitable for receiving signals in accordance with a variety of wireless standards, Wi-Fi, WiMAX, Bluetooth, and various cellular standards. In various embodiments of the subject technology, the receiver 620 may not require any SAW filters and few or no off-chip discrete components such as large capacitors and inductors.

The transmitter 630 may comprise suitable logic circuitry and/or code that may be operable to process and transmit signals from the RF antenna 610. The transmitter 630 may, for example, be operable to up-convert baseband signals to RF signals and amplify RF signals. In various embodiments of the subject technology, the transmitter 630 may be operable to up-convert and amplify baseband signals processed in accordance with a variety of wireless standards. Examples of such standards may include Wi-Fi, WiMAX, Bluetooth, and various cellular standards. In various embodiments of the subject technology, the transmitter 630 may be operable to provide signals for further amplification by one or more power amplifiers.

The duplexer 612 may provide isolation in the transmit band to avoid saturation of the receiver 620 or damaging parts of the receiver 620, and to relax one or more design requirements of the receiver 620. Furthermore, the duplexer 612 may attenuate the noise in the receive band. The duplexer may be operable in multiple frequency bands of various wireless standards.

The baseband processing module 640 may comprise suitable logic, circuitry, interfaces, and/or code that may be operable to perform processing of baseband signals. The baseband processing module 640 may, for example, analyze received signals and generate control and/or feedback signals for configuring various components of the wireless communication device 600, such as the receiver 620. The baseband processing module 640 may be operable to encode, decode, transcode, modulate, demodulate, encrypt, decrypt, scramble, descramble, and/or otherwise process data in accordance with one or more wireless standards.

The processor 660 may comprise suitable logic, circuitry, and/or code that may enable processing data and/or controlling operations of the wireless communication device 600. In this regard, the processor 660 may be enabled to provide control signals to various other portions of the wireless communication device 600. The processor 660 may also control transfers of data between various portions of the wireless communication device 600. Additionally, the processor 660 may enable implementation of an operating system or otherwise execute code to manage operations of the wireless communication device 600. In some aspects, the processor 660 may perform the functionality of the controller discussed above, for example, with respect to FIG. 4.

The memory 650 may comprise suitable logic, circuitry, and/or code that may enable storage of various types of information such as received data, generated data, code, and/or configuration information. The memory 650 may comprise, for example, RAM, ROM, flash, and/or magnetic storage. In various embodiment of the subject technology, information stored in the memory 650 may be utilized for configuring the receiver 620 and/or the baseband processing module 640. In some aspects, the memory 650 may store values of the resistances $R_0$ and $R_g$ and target gas concentrations as discussed above, for example, with respect to FIG. 4.

The local oscillator generator (LOGEN) 670 may comprise suitable logic, circuitry, interfaces, and/or code that may be operable to generate one or more oscillating signals of one or more frequencies. The LOGEN 670 may be operable to generate digital and/or analog signals. In this manner, the LOGEN 670 may be operable to generate one or more clock signals and/or sinusoidal signals. Characteristics of the oscillating signals such as the frequency and duty cycle may be determined based on one or more control signals from, for example, the processor 660 and/or the baseband processing module 640.

In some implementations, the sensor 680 may be a miniature gas sensor of the subject technology, for example, any of the gas sensors 100, 200A, 200B, 200C, 300A, 300B and 400 discussed above with respect to FIGS. 1, 2A-2C. 3A-3B and 4.

In operation, the processor 660 may configure the various components of the wireless communication device 600 based on a wireless standard according to which it is desired to receive signals. Wireless signals may be received via the RF antenna 610 and amplified and down-converted by the receiver 620. The baseband processing module 640 may perform noise estimation and/or noise cancellation, decoding, and/or demodulation of the baseband signals. In this manner, information in the received signal may be recovered and utilized appropriately. For example, the information may be audio and/or video to be presented to a user of the wireless communication device, data to be stored to the memory 650, and/or information affecting and/or enabling operation of the wireless communication device 600. The baseband processing module 640 may modulate, encode and perform other processing on audio, video, and/or control signals to be transmitted by the transmitter 630 in accordance with various wireless standards.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as a "configuration" does not imply that such configuration is essential to the subject technology or that such configuration applies to all configurations of the subject technology. A disclosure relating to a configuration may apply to all configurations, or one or more configurations. A phrase such as a configuration may refer to one or more configurations and vice versa.

The word "example" is used herein to mean "serving as an example or illustration." Any aspect or design described herein as "example" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A miniature gas sensing device, the device comprising:
    a silicon-based substrate including an opening;
    a first membrane formed over the silicon-based substrate, a first portion of the first membrane configured to cover the opening;
    a gas sensing layer formed over a plurality of electrodes disposed over a first surface of the first portion of the first membrane;
    one or more heating elements; and
    a permeable enclosure encapsulating the gas sensing layer and configurable to maintain thermal energy density over the gas sensing layer at a level sufficient to destroy a target gas to allow measuring a zero baseline.

2. The device of claim 1, wherein the permeable enclosure includes one or more restricted flow holes.

3. The device of claim 2, wherein at least one of the one or more restricted flow holes includes a shutter valve mechanism operable to at least partially open or close the one or more restricted flow holes.

4. The device of claim 1, wherein at least one the one or more heating elements or an auxiliary heating element are operable to raise a temperature of a cavity of the permeable enclosure to destroy the target gas and enable zero baseline measurement.

5. The device of claim 4, wherein the one or more heating elements are operable at a nominal temperature and the auxiliary heating element is operable to be turned off to allow a target gas measurement.

6. The device of claim 1, wherein a measured zero baseline corresponds to registering by the gas sensing layer a zero level of measured target gas, and wherein the measured zero baseline enables an absolute target gas measurement.

7. The device of claim 1, wherein the permeable enclosure include one or more notches in one or more sidewalls of the permeable enclosure to allow gas exchange between a cavity of the permeable enclosure and outside of the permeable enclosure.

8. The device of claim 1, wherein the gas sensing layer comprises a permeable coating that allows the target gas to defuse into the gas sensing layer.

9. The device of claim 8, wherein the permeable coating comprises a material with variable electrical resistance, and wherein the variable electrical resistance is variable with a concentration of a defused target gas.

10. The device of claim 1, wherein the permeable enclosure comprises a material with low thermal conductivity including glass.

11. The device of claim 1, wherein the permeable enclosure comprises:
    a glass sidewall surrounding the first portion of the first membrane and being bonded to the silicon-based substrate at a first end of the glass sidewall; and
    a second membrane attached to the glass sidewalls at a second end of the glass sidewall.

12. The device of claim 11, further comprising an auxiliary heating element, wherein the auxiliary heating element is operable to heat up a gas content of the permeable enclosure.

13. The device of claim 11, wherein the second membrane includes one or more restricted flow holes, and wherein an auxiliary heating element is formed over a first side of the second membrane not facing the gas sensing layer, and wherein the one or more heating elements are formed over a second surface the first portion of the first membrane.

14. The device of claim 11, wherein the second membrane is attached to the glass sidewalls by disposing a bonding layer, wherein the bonding layer is partially disposed to leave openings that form one or more restricted flow holes, and wherein the one or more heating elements are formed over a second surface the first portion of the first membrane.

15. The device of claim 11, wherein the second membrane comprise a silicon based double hollow membrane including a plurality of cavities, and wherein at least some of the plurality of cavities have one or more holes.

16. The device of claim 15, wherein at least some of the plurality of cavities are closed cavities, and wherein at least some of the closed cavities are vacuumed and sealed.

17. A miniature gas sensing device, the device comprising:
    a silicon-based substrate including an opening;
    a first membrane formed over the silicon-based substrate, a first portion of the first membrane configured to cover the opening;
    one or more electrodes disposed over a first surface of the first portion of the first membrane;
    a permeable gas sensing layer deposited over the one or more electrodes;
    one or more heating elements formed over a second surface of the first portion of the first membrane;
    a first spacer layer surrounding the first surface of the first portion of the first membrane, a first surface of the first spacer layer being attached to the first membrane; and
    a permeable second membrane attached to a second surface of the first spacer layer to form a first permeable enclosure over the first surface of the first portion of the first membrane, the first permeable enclosure configurable to maintain thermal energy density over the permeable gas sensing layer at a level sufficient to destroy a target gas to allow measuring a zero baseline.

18. The device of claim 17, further comprising at least one of:
 an auxiliary heating element;
 a via coupling the auxiliary heating element through the first spacer layer to conducting traces on the first membrane; and
 a second permeable enclosure similar to the first permeable enclosure formed by a second spacer layer substantially similar to the first spacer layer and a third permeable membrane, the second permeable enclosure being assembled over the permeable second membrane.

19. A miniature gas sensing device, the device comprising:
 a silicon-based substrate including an opening;
 a first membrane formed over the silicon-based substrate, a first portion of the first membrane configured to cover the opening;
 one or more electrodes disposed over a first surface of the first portion of the first membrane;
 a permeable gas sensing coating formed over the one or more electrodes;
 one or more heating elements formed over a second surface of the first portion of the first membrane;
 a spacer layer surrounding the first surface of the first portion of the first membrane, a first surface of the spacer layer being attached to the first membrane; and
 a silicon based double hollow membrane including a plurality of cavities attached to a second surface of the spacer layer.

20. The device of claim 19, wherein at least some of the plurality of cavities have one or more holes, wherein at least some of the plurality of cavities are closed cavities, and wherein at least some of the closed cavities are vacuumed and sealed.

* * * * *